US008834394B2

(12) United States Patent
Ghajar

(10) Patent No.: US 8,834,394 B2
(45) Date of Patent: Sep. 16, 2014

(54) APPARATUS AND METHODS FOR REDUCING BRAIN AND CERVICAL SPINE INJURY

(76) Inventor: Jamshid Ghajar, New York, NY (US)

( * ) Notice: Subject to any disclaimer, the term of this patent is extended or adjusted under 35 U.S.C. 154(b) by 707 days.

(21) Appl. No.: 12/700,035

(22) Filed: Feb. 4, 2010

(65) Prior Publication Data

US 2010/0204628 A1 Aug. 12, 2010

Related U.S. Application Data

(60) Provisional application No. 61/150,480, filed on Feb. 6, 2009.

(51) Int. Cl.

| | | |
|---|---|---|
| *A42B 3/00* | (2006.01) | |
| *F41H 1/04* | (2006.01) | |
| *A61F 5/02* | (2006.01) | |
| *A42B 1/24* | (2006.01) | |
| *A41D 27/26* | (2006.01) | |
| *A61F 5/37* | (2006.01) | |
| *A61F 13/00* | (2006.01) | |
| *A61B 19/00* | (2006.01) | |
| *A61F 5/00* | (2006.01) | |
| *A47C 1/10* | (2006.01) | |
| *A47C 7/36* | (2006.01) | |
| *A61G 15/00* | (2006.01) | |
| *B60R 22/28* | (2006.01) | |
| *A61F 5/055* | (2006.01) | |

(52) U.S. Cl.
CPC ..................................... *A61F 5/055* (2013.01)
USPC .................... 602/18; 2/6.2; 2/6.8; 2/44; 2/45; 2/411; 2/412; 2/421; 2/422; 2/468; 128/846; 128/869; 128/870; 128/874; 128/875; 602/5; 602/17; 297/393; 297/405; 297/465; 297/470

(58) Field of Classification Search
CPC .......... A41B 3/0473; A41B 3/06; A41B 3/12; A41B 3/142; A63B 71/00; A63B 71/08; A63B 71/12; A63B 71/1291; A41D 13/00; A41D 13/015; A61F 5/00; A61F 5/01; A61F 5/05; A61F 5/055; A61F 5/058; A61F 5/05883; A61F 5/02; A61F 5/026; A61F 5/37; A61F 5/3707
USPC .................. 602/5, 17, 18; 128/846, 869, 870, 128/874–875; 2/6.2, 6.8, 44, 45, 411, 412, 2/421, 422, 468; 297/216.12, 216.13, 297/393, 405, 465, 470
See application file for complete search history.

(56) References Cited

U.S. PATENT DOCUMENTS

| | | |
|---|---|---|
| 1,136,307 A | 4/1915 | Bourdon |
| 1,301,276 A | 4/1919 | Kroetz |

(Continued)

FOREIGN PATENT DOCUMENTS

WO WO 2007/120764 A2 10/2007 ................ A61F 5/01

OTHER PUBLICATIONS

International Search Report and Written Opinion, PCT/US07/09028, Nov. 14, 2007, 8 pages.

(Continued)

*Primary Examiner* — Patricia Bianco
*Assistant Examiner* — Brandon L Jackson
(74) *Attorney, Agent, or Firm* — Morgan, Lewis & Bockius LLP

(57) ABSTRACT

In an embodiment, a device for reducing brain and cervical spine injury includes a headpiece sufficiently designed to secure to a user's head, the headpiece having a first attachment member; a support harness sufficiently designed to secure to the user's torso, the support harness having a second attachment member; and a telescoping member having a main tube and a series of progressively smaller diameter tubes nested within each other, wherein the smaller diameter tubes are adapted to extend and compress in a linear plane by the intake and outflow of fluid, wherein the telescoping member has a first engaging member for engaging the first attachment member, and wherein the telescoping member has a second engaging member for engaging the second attachment member.

14 Claims, 8 Drawing Sheets

(56) References Cited

U.S. PATENT DOCUMENTS

| | | | |
|---|---|---|---|
| 1,409,326 A | 3/1922 | Williamson | |
| 3,041,623 A | 7/1962 | Glahe | |
| 3,134,106 A | 5/1964 | Shaffer et al. | |
| 3,148,375 A | 9/1964 | Jones | |
| 3,242,500 A | 3/1966 | Derr | |
| 3,258,010 A | 6/1966 | Austin et al. | |
| 3,471,145 A | 10/1969 | Berger | |
| 3,497,872 A | 3/1970 | Mitchell | |
| 3,671,974 A | 6/1972 | Sims | 2/3 R |
| 3,818,509 A | 6/1974 | Romo et al. | 2/3 R |
| 3,873,996 A | 4/1975 | Varteressian | 2/3 R |
| 3,879,761 A * | 4/1975 | Bothwell | 2/415 |
| 3,889,668 A | 6/1975 | Ochs et al. | 128/134 |
| 3,900,896 A | 8/1975 | Ackerman | 2/2 |
| 4,020,507 A | 5/1977 | Morton | 2/411 |
| 4,219,193 A | 8/1980 | Newman | 272/94 |
| 4,338,685 A | 7/1982 | LaPorta, Jr. | 2/2 |
| 4,489,919 A | 12/1984 | Ostrobrod | 254/346 |
| 4,501,023 A | 2/1985 | Bilberry | 2/2 |
| 4,638,510 A | 1/1987 | Hubbard | 2/6 |
| 4,664,341 A * | 5/1987 | Cummings | 244/122 AG |
| 4,697,289 A | 10/1987 | Luigi | 2/422 |
| 4,825,476 A | 5/1989 | Andrews | 2/421 |
| 4,846,313 A | 7/1989 | Sharp | 188/187 |
| 4,909,459 A | 3/1990 | Patterson | 244/122 |
| 4,945,305 A | 7/1990 | Blood | |
| 5,027,833 A | 7/1991 | Calkin | 128/870 |
| 5,123,408 A | 6/1992 | Gaines | 602/17 |
| 5,210,894 A * | 5/1993 | Minton | 5/637 |
| 5,219,206 A | 6/1993 | Anthony et al. | 297/473 |
| 5,242,377 A | 9/1993 | Boughner et al. | 602/17 |
| 5,248,293 A | 9/1993 | Hubbard et al. | 602/17 |
| 5,261,125 A | 11/1993 | Cartwright et al. | 2/421 |
| 5,287,562 A * | 2/1994 | Rush, III | 2/413 |
| 5,313,670 A * | 5/1994 | Archer, III | 2/411 |
| 5,314,404 A | 5/1994 | Boughner et al. | 602/17 |
| 5,329,933 A | 7/1994 | Graf | |
| 5,336,138 A * | 8/1994 | Arjawat | 482/10 |
| 5,338,062 A | 8/1994 | Kiuchi et al. | 280/735 |
| 5,371,905 A * | 12/1994 | Keim | 2/413 |
| 5,433,201 A | 7/1995 | Manthey | |
| 5,437,613 A | 8/1995 | Reggio et al. | 602/18 |
| 5,517,699 A | 5/1996 | Abraham, II | 2/425 |
| 5,546,601 A | 8/1996 | Abeyta | 2/2 |
| 5,581,816 A * | 12/1996 | Davis | 2/416 |
| 5,715,541 A | 2/1998 | Landau | 2/425 |
| 5,920,395 A | 7/1999 | Schulz | |
| 5,930,843 A | 8/1999 | Kelly | 2/468 |
| 5,955,879 A | 9/1999 | Durdle et al. | |
| 6,006,368 A | 12/1999 | Phillips | 2/468 |
| 6,009,566 A | 1/2000 | Hubbard | 2/468 |
| 6,052,835 A | 4/2000 | O'Shea | 2/468 |
| RE36,691 E | 5/2000 | Pinsen | 2/468 |
| 6,126,043 A * | 10/2000 | Albert, II | 222/340 |
| 6,330,722 B1 | 12/2001 | Betts | 2/416 |
| 6,385,781 B1 | 5/2002 | Rose et al. | 2/425 |
| 6,418,564 B1 | 7/2002 | Sheridan | 2/425 |
| 6,481,026 B1 | 11/2002 | McIntosh | 2/468 |
| 6,751,809 B1 | 6/2004 | Cooper et al. | 2/421 |
| 6,874,170 B1 | 4/2005 | Aaron | 2/468 |
| 6,931,669 B2 | 8/2005 | Ashline | 2/422 |
| 6,968,576 B2 | 11/2005 | McNeil et al. | 2/425 |
| 6,971,123 B2 | 12/2005 | Weaver | 2/468 |
| 6,978,523 B2 | 12/2005 | Downing et al. | 24/628 |
| 6,984,208 B2 | 1/2006 | Zheng | |
| 7,120,982 B2 | 10/2006 | Downing et al. | 29/401.1 |
| 7,155,747 B2 * | 1/2007 | Baker | 2/422 |
| 7,165,785 B2 | 1/2007 | Bouladian | 280/735 |
| 7,210,240 B2 | 5/2007 | Townsend et al. | |
| 7,231,698 B2 | 6/2007 | Downing et al. | 24/628 |
| 7,234,210 B2 | 6/2007 | Stiles et al. | 24/628 |
| 7,387,598 B2 | 6/2008 | Miller | 482/112 |
| 7,426,773 B2 | 9/2008 | Downing et al. | 24/628 |
| 8,181,281 B2 * | 5/2012 | Nagely et al. | 2/425 |
| 2003/0088906 A1 * | 5/2003 | Baker | 2/416 |
| 2004/0194194 A1 * | 10/2004 | McNeil et al. | 2/421 |
| 2005/0177065 A1 | 8/2005 | Ghajar | |
| 2007/0186239 A1 * | 8/2007 | Briggs | 725/39 |
| 2007/0186329 A1 | 8/2007 | Baker | 2/410 |
| 2007/0245464 A1 * | 10/2007 | Baker | 2/411 |
| 2008/0209617 A1 * | 9/2008 | Castillo | 2/461 |
| 2009/0064396 A1 | 3/2009 | Ghajar | 2/411 |
| 2009/0158509 A1 | 6/2009 | Ghajar | 2/422 |
| 2013/0131554 A1 | 5/2013 | Dunias et al. | |

OTHER PUBLICATIONS

HANS Device, en.wikipedia.org/wiki/HANS_device, Wikipedia—the free encyclopedia, downloaded Apr. 11, 2009, 5 pages.

Ghajar, Communication pursuant to Article 94(3) EPC, EP 06813639.9, May 3, 2013, 5 pgs.

Schalen, Quantification of tracking eye movements in normal subjects, ACTA OTO-LARYNGOLOGICA Nov.-Dec. 1990, vol. 90, No. 5-6, Nov. 1980, pp. 404-413.

Amann, Laser Ranging: a critical review of usual techniques for distance measurement, Op. Eng 40(1), Jan. 10-19, 2001, pp. 10-19.

Anonymous, A Library of Textile Sensors: Capturing Movement and Touch with Fabric, Apr. 18, 2011, 9 pgs.

Benet, Using infrared sensors for distance measurement in mobile robots, Robotics and Autonomous Systems 1006 (2002), 12 pgs.

Gallagher, An Efficient Real-Time Human Posture Tracking Algorithm Using Low-Cost Inertial and Magnetic Sensors, Proc. Int'l. Conference on Intelligent Robots and Systems, Sendai, JP, Sep. 28-Oct. 2, 2004, pp. 2967-2972.

Klotz, 24GHz Radar Sensors for Automotive Applications, Technical Univ. of Hamburg-Harburg, May 1999, pp. 359-362.

* cited by examiner

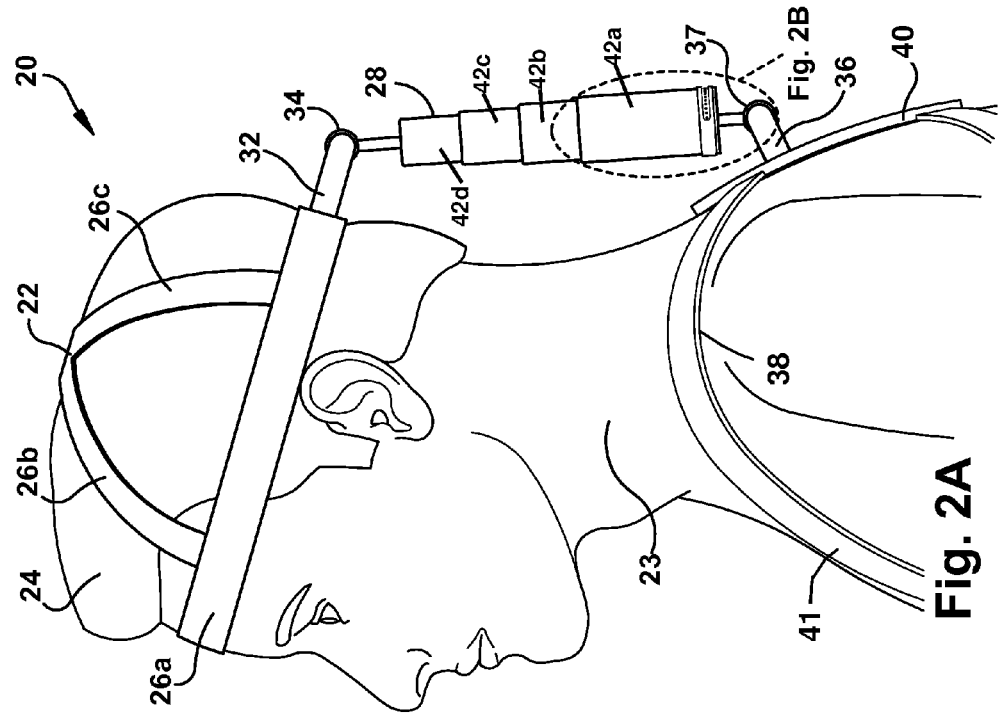
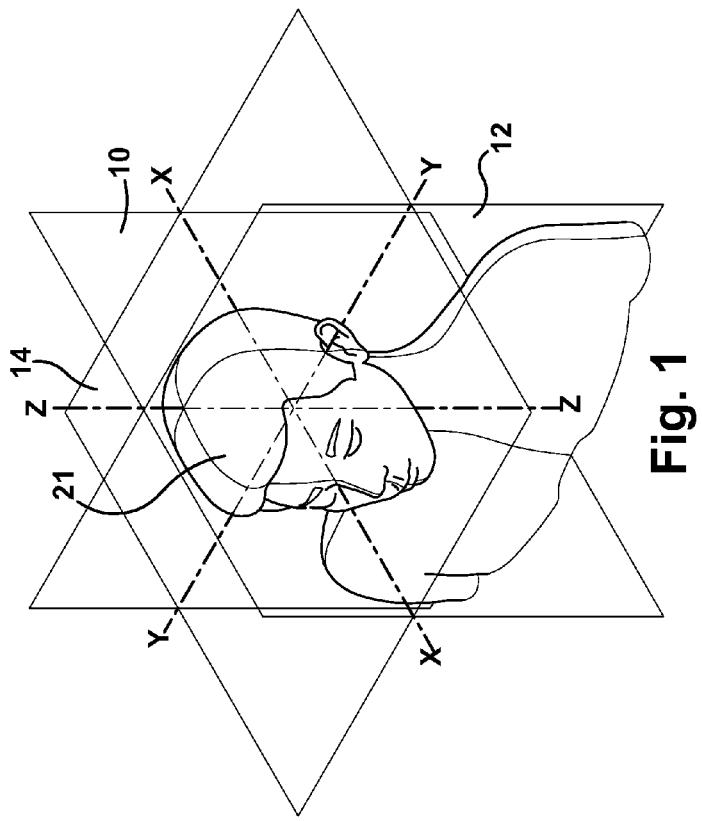

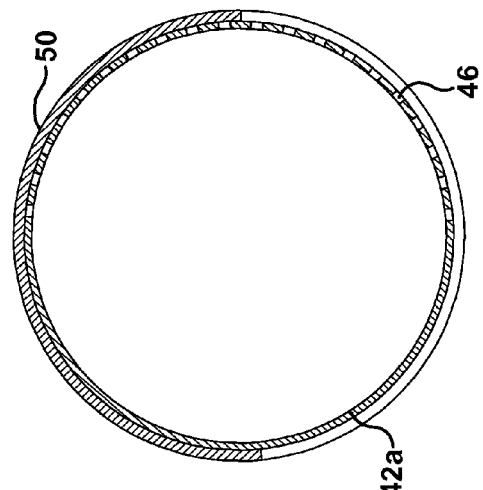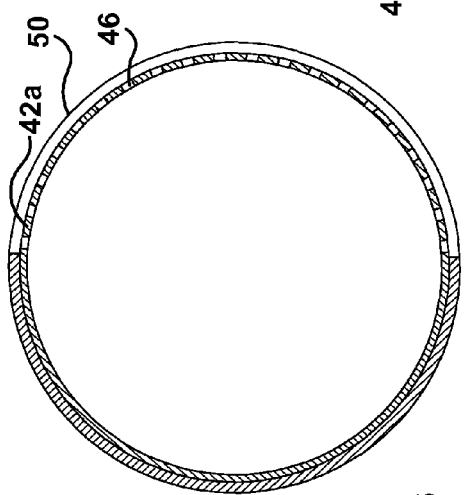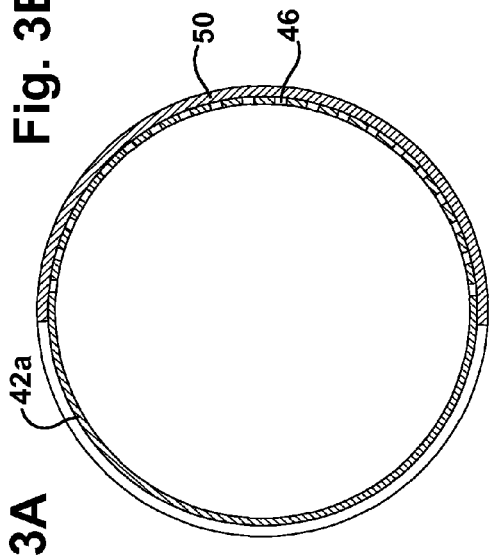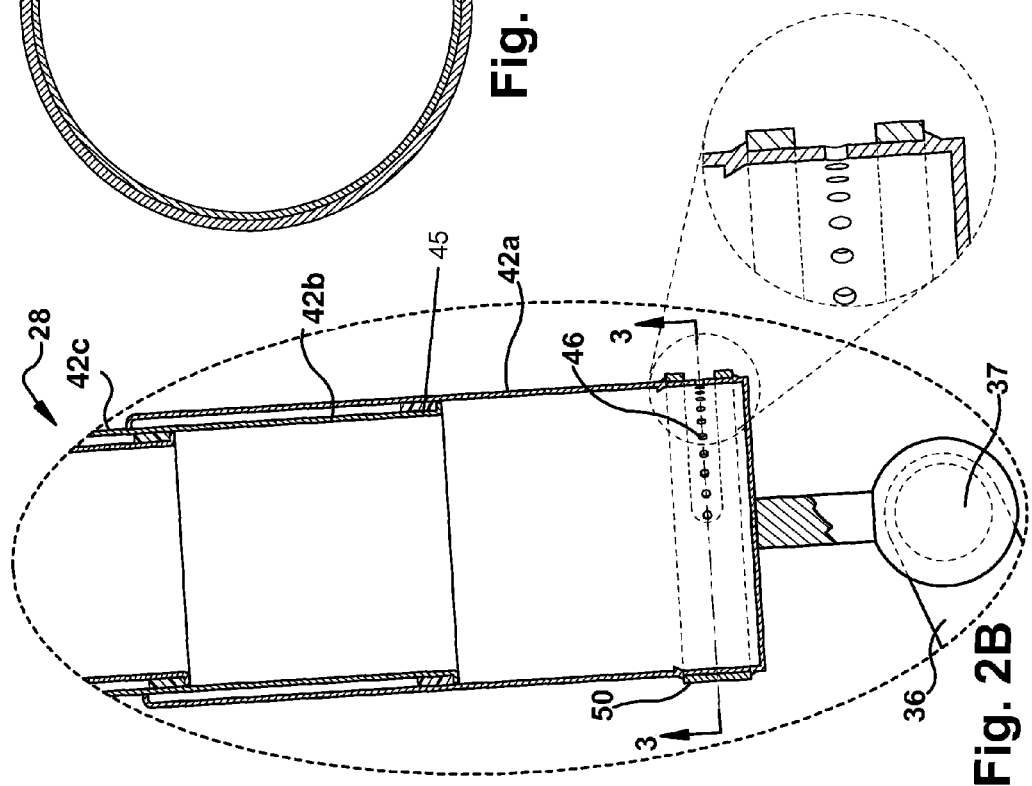

US 8,834,394 B2

APPARATUS AND METHODS FOR REDUCING BRAIN AND CERVICAL SPINE INJURY

RELATED APPLICATION

This application claims the benefit of and priority to U.S. Provisional Application Ser. No. 61/150,480, filed Feb. 6, 2009, the entirety of this application is hereby incorporated herein by reference.

FIELD

The present disclosure relates to devices for reducing brain and cervical spine injury, and more particularly to devices and methods for preventing the head from substantial rotational acceleration or deceleration that could lead to tearing of brain or cervical spine tissue.

BACKGROUND

Rapid acceleration and deceleration of a person's head, especially with a rotational component, can cause shearing damage to the white matter that connects neurons in the brain, resulting in concussion symptoms, and even coma, when the shearing is severe. Disruption of white matter connections disables brain function. Symptoms can be as mild as memory and attention difficulties, and as serious as a coma state. This is the most common form of brain injury and has been shown to occur in car crashes, falls, sporting accidents and combat as a consequence of road-side bombs that cause a blast wave to whip the head producing rotational shear injury. In addition, high acceleration and rapid deceleration in flexion, extension or rotation movements can cause cervical spine fractures, torn ligaments, disc herniations, spinal cord injury and other damage of the neck. Rapid rotation and whiplash of the head is exaggerated by the flexibility of the neck, which is unable to effectively resist sudden loads, whether the load is from an impact, rapid deceleration or a blast wave. These sudden skull rotations can induce the brain to move inside the skull, stretching or tearing tissue within the white matter of the brain through inertial effects.

SUMMARY

Devices and methods for reducing brain and cervical spine injury are disclosed herein.

According to the aspects illustrated herein, there is provided a device that includes a headpiece sufficiently designed to secure to a user's head, the headpiece having a first attachment member; a support harness sufficiently designed to secure to the user's torso, the support harness having a second attachment member; and a telescoping member having a main tube and a series of progressively smaller diameter tubes nested within each other, wherein the smaller diameter tubes are adapted to extend and compress in a linear plane by the intake and outflow of fluid, wherein the telescoping member has a first engaging member for engaging the first attachment member, and wherein the telescoping member has a second engaging member for engaging the second attachment member, wherein the first engaging member and the first attachment member form a ball and socket joint adapted to allow three degrees of freedom, permitting rotary movement in all directions through the movement of the first engaging member in the first attachment member, and wherein the second engaging member and the second attachment member form a ball and socket joint adapted to allow three degrees of freedom, permitting rotary movement in all directions through the movement of the second engaging member in the second attachment member. In an embodiment, the first engaging member of the telescoping member connects with the first attachment member of the headpiece approximately at a level of the user's inion. In an embodiment, the second engaging member of the telescoping member connects with the second attachment member of the support harness approximately at a level of the user's C7/T1 spinous processes.

According to the aspects illustrated herein, there is provided a device that includes a headpiece sufficiently designed to secure to a user's head, the headpiece having a first attachment member; a support harness sufficiently designed to secure to the user's torso, the support harness having a second attachment member; and a telescoping member having expansion bellows adapted to extend and compress in a linear plane by the intake and outflow of fluid, wherein the telescoping member has a first engaging member for engaging the first attachment member, and wherein the telescoping member has a second engaging member for engaging the second attachment member, wherein the first engaging member and the first attachment member form a ball and socket joint adapted to allow three degrees of freedom, permitting rotary movement in all directions through the movement of the first engaging member in the first attachment member, and wherein the second engaging member and the second attachment member form a ball and socket joint adapted to allow three degrees of freedom, permitting rotary movement in all directions through the movement of the second engaging member in the second attachment member. In an embodiment, the first engaging member of the telescoping member connects with the first attachment member of the headpiece approximately at a level of the user's inion. In an embodiment, the second engaging member of the telescoping member connects with the second attachment member of the support harness approximately at a level of the user's C7/T1 spinous processes.

According to aspects illustrated herein, there is provided a method for preventing brain and cervical spine injury that includes providing a device comprising a headpiece sufficiently designed to secure to the user's head, the headpiece having a first attachment member; a support harness sufficiently designed to secure to the user's torso, the support harness having a second attachment member; an acceleration threshold device sufficiently designed to detect external forces experienced by the user's head and for providing an output signal to a processor circuit; and a telescoping member adapted to extend and compress in a linear plane by the intake and outflow of fluid, wherein the telescoping member has a first engaging member for engaging the first attachment member, the first engaging member and the first attachment member forming a ball and socket joint adapted to allow three degrees of freedom, permitting rotary movement in all directions through the movement of the first engaging member in the first attachment member, and wherein the telescoping member has a second engaging member for engaging the second attachment member, the second engaging member and the second attachment member forming a ball and socket joint adapted to allow three degrees of freedom, permitting rotary movement in all directions through the movement of the second engaging member in the second attachment member; connecting the first engaging member of the telescoping member with the first attachment member of the headpiece approximately at a level of the user's inion; connecting the second engaging member of the telescoping member with the second attachment member of the support harness approximately at a level of the user's C7/T1 spinous processes;

detecting, using an acceleration threshold detector, external contact forces experienced by the user's head to determine acceleration of the user's head; providing, using the acceleration threshold detector, an output signal representing if the determined acceleration experienced by the user's head reached a predetermined threshold; receiving, using a processor, the output signal from the acceleration threshold detector; and generating, using the processor, an event signal to trigger the intake or outflow of fluid by the telescoping member in response to the determined acceleration.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1 shows a front view of the three rotational planes, coronal (Y), axial (X) and sagittal (Z) planes or axes, through a person's head.

FIG. 2A shows a side view of an embodiment of a device of the present disclosure in a neutral position on a user. The device includes a headpiece, a support harness and a telescoping member having a main tube and a series of progressively smaller diameter tubes nested within each other.

FIG. 2B shows an exploded view of the telescoping member of FIG. 2A. The telescoping member includes perforated portions allowing entry and exit of fluid into and out of the telescoping member and an outer rotatable circular member for controlling the entry and exit of fluid through the perforated portions. The inset shows a close-up view of the relationship between the perforated portions of the telescoping member and the outer circular member.

FIG. 3A, FIG. 3B and FIG. 3C show cross-sectional views of the telescoping member of FIG. 2B taken along line 3-3. FIG. 3A shows the outer circular member in a fully open position, allowing complete fluid flow into and out of the telescoping member. FIG. 3B shows the outer circular member in a partially open position, allowing partial fluid flow into and out of the telescoping member. FIG. 3C shows the outer circular member in a closed position, inhibiting fluid flow into and out of the telescoping member.

Figure 5:
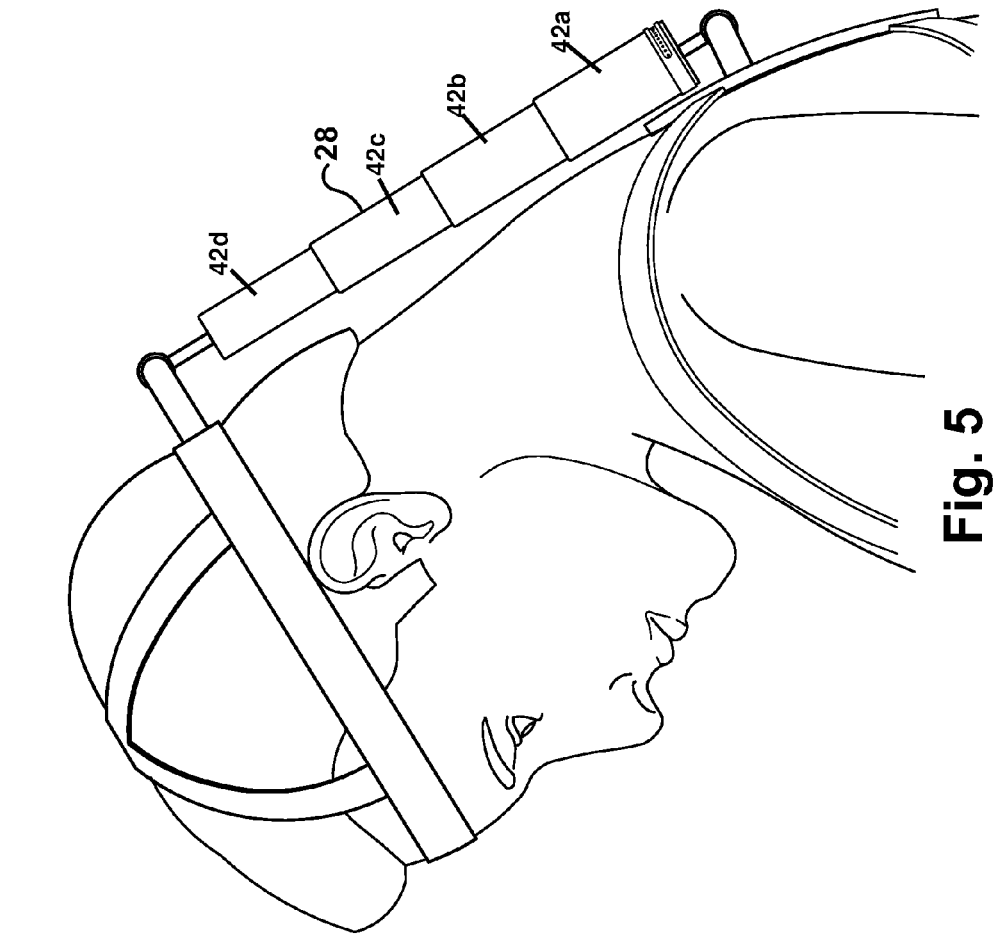
FIG. 5 shows a side view of the device of FIG. 2A on the user. The telescoping member is in a fully extended state.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Devices and methods for reducing brain and cervical spine injury are disclosed herein. The devices disclosed herein can be use to protect the brain, the cervical spine, and/or the spinal cord from high accelerations and rapid decelerations of the head in all axes. In an embodiment, a device of the present disclosure is a neck bracing system that allows normal motion of the head, but dampens head movement in response to rapid acceleration or decelerations at a threshold that would produce brain injury, cervical spine, or spinal cord injury.

FIG. 1 shows the three planes in which a person's head 21 can rotate. The coronal plane 12 lies roughly parallel to the chest. Moving the head 21 side to side, or moving the ear toward the shoulder, is an example of head rotation in the coronal plane 12. The axial plane 14 perpendicular to coronal plane 12 lies roughly parallel to the top of the head 21, like the rim of a hat. Shaking one's head to indicate "no, is an example of rotation in the axial plane 14. The sagittal plane 10 is perpendicular to both planes 12 and 14, and bisects the left side of the head 21 from the right. Nodding one's head to indicate, "Yes," is an example of rotation in the sagittal plane 10.

An embodiment of a device 20 of the present disclosure for reducing brain and cervical spine injury is shown in the various illustrations of FIGS. 2A-8. As illustrated in FIG. 2A, the device 20 includes a headpiece 22 for securing to a person's head 24. In the embodiment depicted in FIG. 2A, the headpiece 22 is a head harness composed of interconnected straps 26a, 26b and 26c. The straps 26a, 26b and 26c can be made out of leather, plastic, cloth, rubber and any other material as the present disclosure is not intended to be limited in this manner. As illustrated in FIG. 2A, one strap 26a is positioned circumferentially about the head 24, and two straps 26b and 26c, are positioned in a criss-cross manner on top of the head 24. In an embodiment, there may be more or less straps for securing to the head 24 as the present disclosure is not intended to be limited in this manner. The straps 26a, 26b and 26c can be positioned in different arrangements on or around the head 24 and still be within the scope of the presently disclosed embodiments. The straps 26a, 26b and 26c can be fabricated from one single material or out of multiple pieces of material that are engaged together. The headpiece 22 includes a first attachment member 32 located at a rear of the strap 26a. In an embodiment, the first attachment member 32 attaches to the strap 26a at the back of the head 24 at approximately the level of the inion.

Although the embodiments depicted in FIGS. 2A-8 show the headpiece 22 as a head harness, other headpieces can be used with the device 20. In an embodiment, a headpiece for use with the device 20 is a helmet having the appearance of a conventional football helmet. The helmet may be made out of plastic, rubber, wood or any other material as the present disclosure is not intended to be limited in this manner. In an embodiment, the helmet may not include facial protection or straps for securing the helmet to the head 24. In an embodiment, the headpiece 22, designed as a head harness, a helmet or any other similar type device, is sufficiently designed to only secure to a user's head and does not need to be secured to any other components such as, for example, components of a moving vehicle or sports training gear, to produce the desired protection.

As further shown in FIG. 2A and FIG. 2B, the device 20 includes a telescoping member 28 comprising a series of four tubes 42a, 42b, 42c and 42d of progressively smaller diameters nested within each other. It should be understood that although four segments are shown in the various figures, the telescoping member 28 may include any suitable number of tubes. In an embodiment, the telescoping member 28 is a piston-like telescoping member. The largest diameter sleeve 42a is called the main or barrel, and the smaller inner sleeves 42b, 42c and 42d are called the stages or cylindrical tubular sliding members, each stage having a successively smaller diameter than the preceding stage. The smallest stage 42d is also known as the plunger. When the telescoping member 28 is in the retracted position, the stages 42b, 42c and 42d are nested within one another in the barrel 42a. As the telescoping member 28 is extended, each nested stage 42b, 42c and 42d emerges from it's neighbor and extends to it's full length. In an embodiment, the telescoping member 28 defines a variable volume chamber, where the chamber has a minimum volume when the stages 42b, 42c and 42d are nested within one another, and the chamber has a maximum volume when the stages 42b, 42c and 42d are extended. The stages 42b, 42c and 42d of the telescoping member 28 may extend and compress freely during voluntary head movements and may extend and compress at reduced rates during high accelerations and rapid decelerations. The telescoping member 28 may be made out of plastic, steel, metal or any other light weight material to minimize bending of the member and allow for easy carrying.

The telescoping member 28 is sufficiently designed for extension and compression in a linear plane, and includes a first engaging member or connector 34 for engaging the first attachment member 32 of the headpiece 22, and a second engaging member or connector 37 for engaging a second attachment member 36 of a support harness 38. In an embodiment, the connector 34 is a universal joint, allowing free movement in at least 180 degrees so that the telescoping member 28 remains linear. In an embodiment, the connector 34 and the first attachment member 32 attach to the strap 26a at the back of the head 24 at approximately the level of the inion. The inion represents the middle of the back of the head 24 and additionally is located equidistantly from bottom of skull to top. The connector 34 may be detachable or removable from the first attachment member 32. The connector 34 may be fabricated from a joint, a hinge, a socket or any other device for coupling the headpiece 22 to the telescoping member 28 and allowing movement in more than one plane. In an embodiment, the connector 34 and the first attachment member 32 form a ball and socket joint allowing three degrees of freedom, permitting rotary movement of the head 24 in all directions through the movement of the connector 34 in the first attachment member 32. In such embodiments, the connector 34 terminates in a ball, and the first attachment member 32 terminates in a spherical shell sized to snugly envelope the ball of the connector 34. When the ball of the connector 34 is within the socket of the first attachment member 32, the centers of the ball and socket are coincident, resulting in a spherical geometry that facilitates full three dimensional rotation of the connector 34 and the first attachment member 32 about the coincident centers, providing multi-axial and multi-directional positioning of the head 24. In an embodiment, this full three dimensional rotation allows the head 24 to move in any direction in coronal, sagittal and axial planes, producing no bending force on the telescoping member 28, allowing the telescoping member 28 to function only in compression and extension. In an embodiment, the ball and socket joint allows free movement of the telescoping member 28 such that the telescoping member 28 remains in straight alignment and does not bend. In an embodiment, the connector 34 is made from a pliable material.

In an embodiment, the support harness 38 includes a vest or plate portion 40 and straps 41 sufficiently designed to secure to the user's torso. In an embodiment, the support harness 38 may include a chest vest. In an embodiment, the support harness 38, designed as a vest with straps, a chest vest or any other similar type device, is sufficiently designed to only secure to a user's torso and does not need to be secured to any other components such as, for example, components of a moving vehicle or sports training gear, to produce the desired protection. In an embodiment, the connector 37 attaches to the plate portion 40 of the support harness 38 at the level of the C7/T1 spinous processes. The C7/T1 spinous processes represents the top or the torso and the base of the neck 23. The connector 37 may be detachable or removable from the second attachment member 36. The connector 37 may be fabricated from a joint, a hinge, a socket or any other device for coupling the support harness 38 to the telescoping member 28 and allowing movement in more than one plane. In an embodiment, the connector 37 and the second attachment member 36 form a ball and socket joint allowing three degrees of freedom, permitting rotary movement of the head 24 in all directions through the movement of the connector 37 in the second attachment member 36. In such embodiments, the connector 37 terminates in a ball, and the second attachment member 36 terminates in a spherical shell sized to snugly envelope the ball of the connector 37. When the ball of the connector 37 is within the socket of the second attachment member 36, the centers of the ball and socket are coincident, resulting in a spherical geometry that facilitates full three dimensional rotation of the connector 37 and the second attachment member 36 about the coincident centers, providing multi-axial and multi-directional positioning of the head 24. In an embodiment, this full three dimensional rotation allows the head 24 to move in any direction in coronal, sagittal and axial planes, producing no bending force on the telescoping member 28, allowing the telescoping member 28 to function only in compression and extension. In an embodiment, the ball and socket joint allows free movement of the telescoping member 28 such that the telescoping member 28 remains in straight alignment and does not bend. In an embodiment, the connector 37 is made from a pliable material. In an embodiment, a support harness 38 is not included as part of the device 20. In such embodiments, the connector 37 can attach to a second attachment member on an external component, such as, for example, a second attachment member of a car seat in a vehicle that the user is in. In such embodiments, the connector 37 and the second attachment member form a ball and socket joint allowing three degrees of freedom, permitting rotary movement in all directions through the movement of the connector 27 in the second attachment member.

The telescoping member 28 may compress the distance between the inion and first thorasic spinous process when the head 24 and neck 23 are fully extended, which is approximately two inches, and may extend the distance, about 8 inches, between the inion and first thoracic spinous process when the head 24 and neck 23 are fully in flexion, which is approximately eight inches. The telescoping member 28 remains linear during extension and compression. In an embodiment, the telescoping member 28 includes a gas spring piston damper, a lockable gas spring piston damper with a locking device, a dynamic gas spring piston damper with a damping device or any other type of piston damper as the present disclosure is not intended to be limited in this manner.

FIG. 2B shows an exploded view of the telescoping member 28 showing sliding members 42a, 42b and 42c. In an embodiment, the telescoping member 28 extends and compresses by the intake/outflow of fluid through the telescoping member 28. In an embodiment, the fluid powering the telescoping member 28 is a gas. In an embodiment, the gas is air. In an embodiment, the fluid powering the telescoping member 28 is a liquid. In an embodiment, the liquid is a hydraulic liquid. In embodiments where the fluid powering the telescoping member 28 is a liquid, the telescoping member 28 may further comprise an airtight flexible membrane adapted to house liquid under pressure. The flexible membrane covers the inside surface of the stages and constitutes a completely sealed chamber having the liquid material therein under pressure. In embodiments where the telescoping member 28 is powered by a liquid, a container or bag may be provided and is adapted to house the liquid when the liquid is not within the flexible membrane of the telescoping member 28. The container or bag housing the liquid can be in fluid communication with the perforated portions 46 of the telescoping member 28.

The rate of fluid exchange into and out of the telescoping member 28 can be controlled using a number of voluntary or programmed cues. Perforated portions 46 of the telescoping member 28 allow entrance and exit of fluid during extension and compression of the telescoping member 28. In an embodiment, the telescoping member 28 includes gaskets 45 positioned above the perforated portions 46 keep the telescoping member 28 airtight and to prevent fluid from entering between the sliding members 42b, 42c and 42d. The perforated portions 46 may be variably exposed by an overriding rotatable circular member 50 surrounding an outer diameter of the main tube 42a of the telescoping member 28. The outer circular member 50 can expose more or less of the perforated portions 46 as needed at the base of the telescoping member 28. In an embodiment, the outer circular member 50 can be controlled manually by turning the outer circular member 50 and exposing more or less of the perforated portions 46. In an embodiment, the outer circular member 50 can be controlled electronically. The inset shown in FIG. 2B shows a close-up view of the relationship between the perforated portions 46 of the telescoping member 28 and the outer circular member 50. In an embodiment, the outer circular member 50 may be in an entirely open position as shown in FIG. 3A where fluid may completely enter and exit the perforated portions 46, or may be in a partially open position as shown in FIG. 3B where fluid may enter and exit the perforated portions 46 at a reduced rate, or may be in an entirely closed position as shown in FIG. 3C where no fluid may enter or exit the perforated portions 46.

In an embodiment, the outer circular member 50 is controlled electronically to expose more or less of the perforated portions 46. In such embodiments, the outer circular member 50 can be controlled by an acceleration sensor arrangement comprising an acceleration threshold detector for detecting external forces experienced by the user's head to determine acceleration of the user's head and for providing an output signal; and a processor for receiving the output signal and generating an event signal to trigger the intake or outflow of fluid by the telescoping member 28 by moving the outer circular member 50 to expose more or less of the perforated portions 46. In an embodiment, the acceleration threshold detector provides an output signal having a first value when the acceleration is less than a predetermined threshold and is arranged to switch the output signal from the first value to a second value when the acceleration reaches the predetermined threshold. The processor generates an event signal to trigger movement of the outer circular member 50 to expose more or less of the perforated portions 46, in response to the output signal from the acceleration threshold detector switching to the second value. In an embodiment, the acceleration threshold detector comprises at least one of a piezo element and a micromachined element. In an embodiment, the acceleration threshold detector is a Piezoresisitive 3-Axis acceleration sensor adapted to trigger an event (such as the intake or outflow or air by the telescoping member) when all outputs from X, Y or Z go below a predetermined set threshold. In an embodiment, the acceleration threshold detector is a MEMS accelerometer. A programmable sequence can control the movement of the outer circular member 50 to expose more or less of the perforated portions 46 such that at the predetermined threshold of acceleration there is a shut off of the fluid portal followed by a rapid release and then closure, repeating hundreds of times per second causing an oscillatory slowing of the acceleration to a full stop. If the head movement exceeds the set threshold then there is a rapid deceleration to return the movement to below threshold acceleration. Once set at a threshold, an accelerometer can activate the locking device in a lockable gas spring piston damper or the damping device in a dynamic gas spring piston damper. In an embodiment, the accelerometer may be set at a threshold of about 20 g or less or 3000 rads/second squared or less. Setting the accelerometer at this threshold may aid in preventing or ameliorating the chances of sustaining a concussion. In an embodiment, a pressure sensor integrator (rate of pressure increase and decrease) or air velocity measurement may be used in conjunction with the telescoping member 28 to set various thresholds to activate the locking device in a lockable gas spring piston damper or the damping device in a dynamic gas spring piston damper. In an embodiment, the device 20 may include an acceleration threshold detector with a set acceleration threshold and an electronic shut-off valve. In an embodiment, the acceleration threshold detector may be located on the front at a point between the eyes and mid forehead to detect acceleration in the coronal, sagittal and axial planes. When located vertically on the front, the acceleration threshold detector may detect acceleration on the sagittal plane. When located horizontally on the front, the acceleration threshold detector may detect acceleration on the axial plane. In an embodiment, the acceleration threshold detector may be located vertically at a point above the ear. This location may allow acceleration to be detected in the coronal plane.

Figure 4:
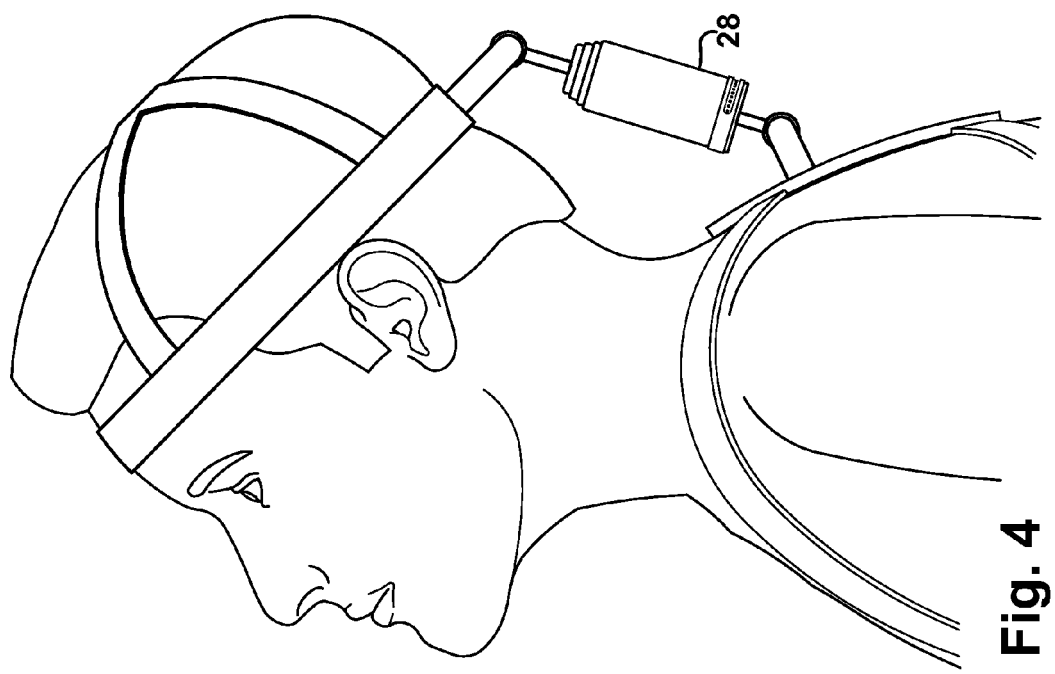
FIG. 4 shows a side view of the device of FIG. 2A on the user. The telescoping member is in a fully compressed state.
Figure 7:
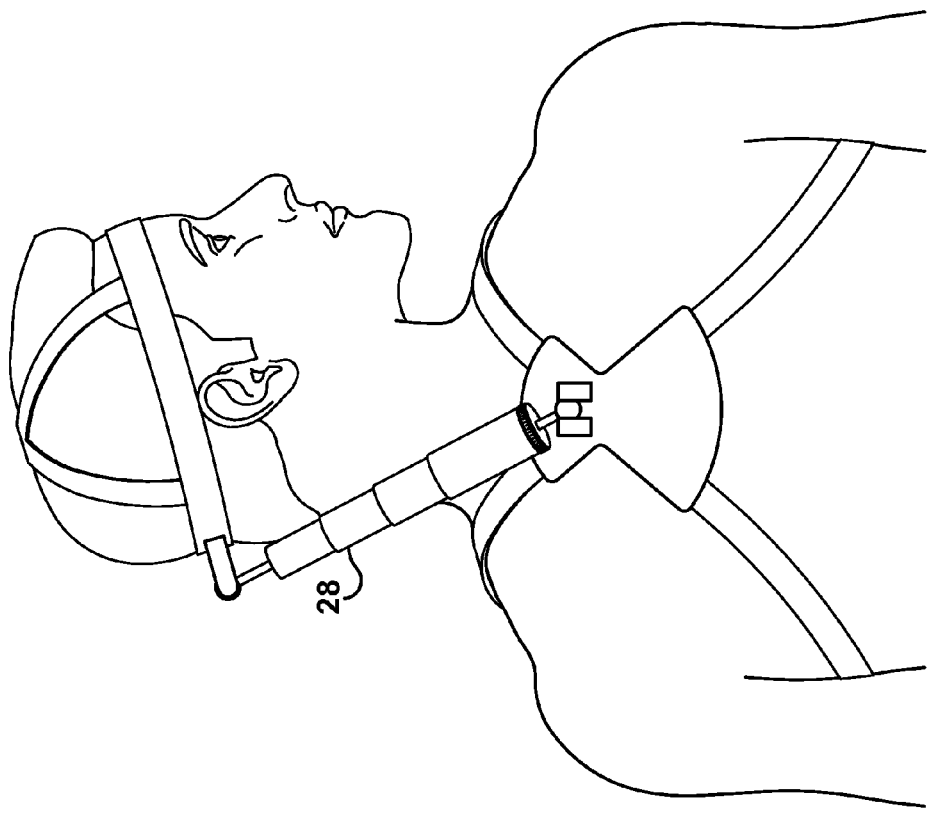
FIG. 7 shows a rear view of the device of FIG. 2A on the user. The telescoping member is in an extended position as the user's head is turned in the axial plane.
Figure 6:
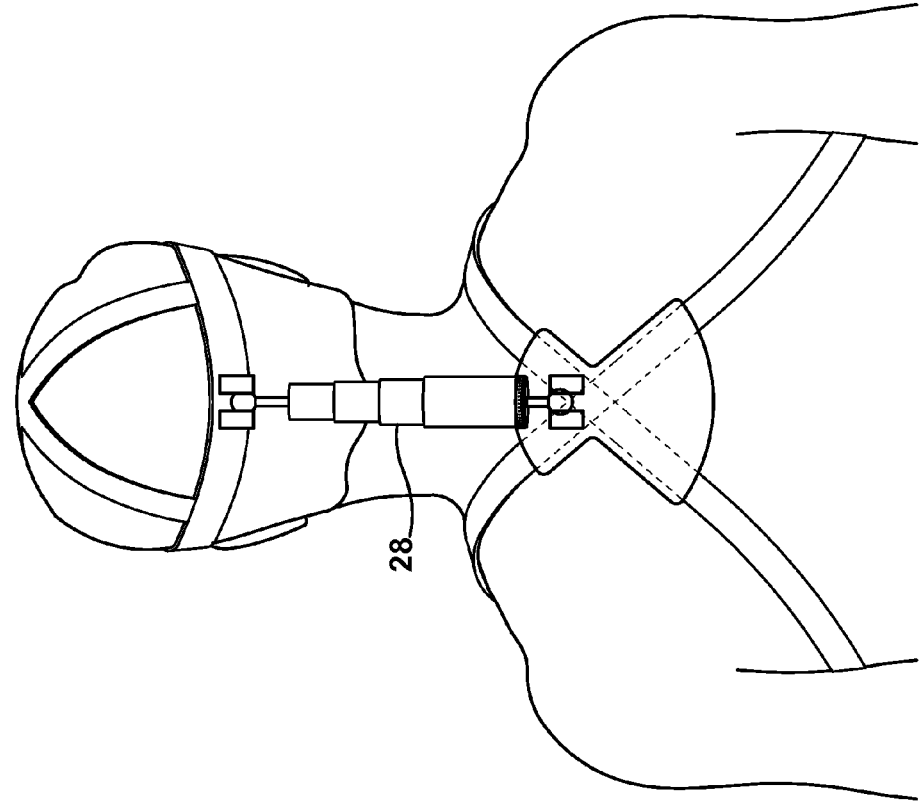
FIG. 6 shows a rear view of the device of FIG. 2A on the user. The telescoping member is in a neutral position.
Figure 8:
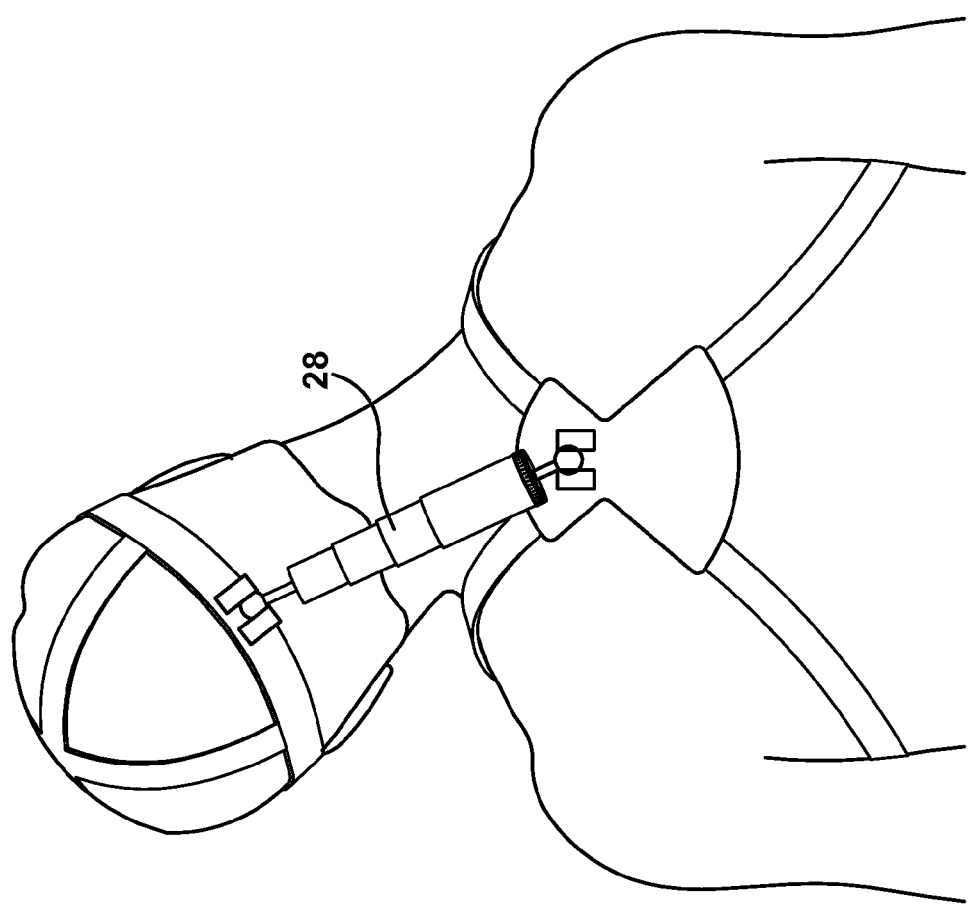
FIG. 8 shows a rear view of the device of FIG. 2A on the user. The telescoping member is in an extended position as the user's head is turned in the coronal plane.

FIGS. 4-8 show the device 20 of FIG. 2A during various head movements. The device 20 provides unencumbered head motion and range during normal circumstances. The sliding members 42b, 42c and 42d are of substantially the same length, so that they can be moved from an outstretched position, such as shown in FIG. 5, to a substantially fully telescoped or compressed position, such as shown in FIG. 4. FIG. 4 shows the telescoping member 28 fully compressed with the head 24 and the neck 23 in a fully extended position. In the outstretched position, the inner ends of the sliding members are adjacent one another. FIG. 5 shows the head 24 and the neck 23 in full flexion with the telescoping member 28 in full extension. In the telescoped position, the inner ends of the sliding members are adjacent the outer ends of the other tube. FIG. 6 shows a rear view of the telescoping member 28 in a neutral position attached to the strap 26a at the back of the head 24 at approximately the level of the inion and attached to the support harness 38 at the level of the C7/T1 spinous processes. FIG. 7 shows the telescoping member 28 extended as the head 24 is turned in the axial plane. FIG. 8 shows the telescoping member 28 extended as the head 24 is bent in the coronal plane so the ear approaches the shoulder.

Figure 9:
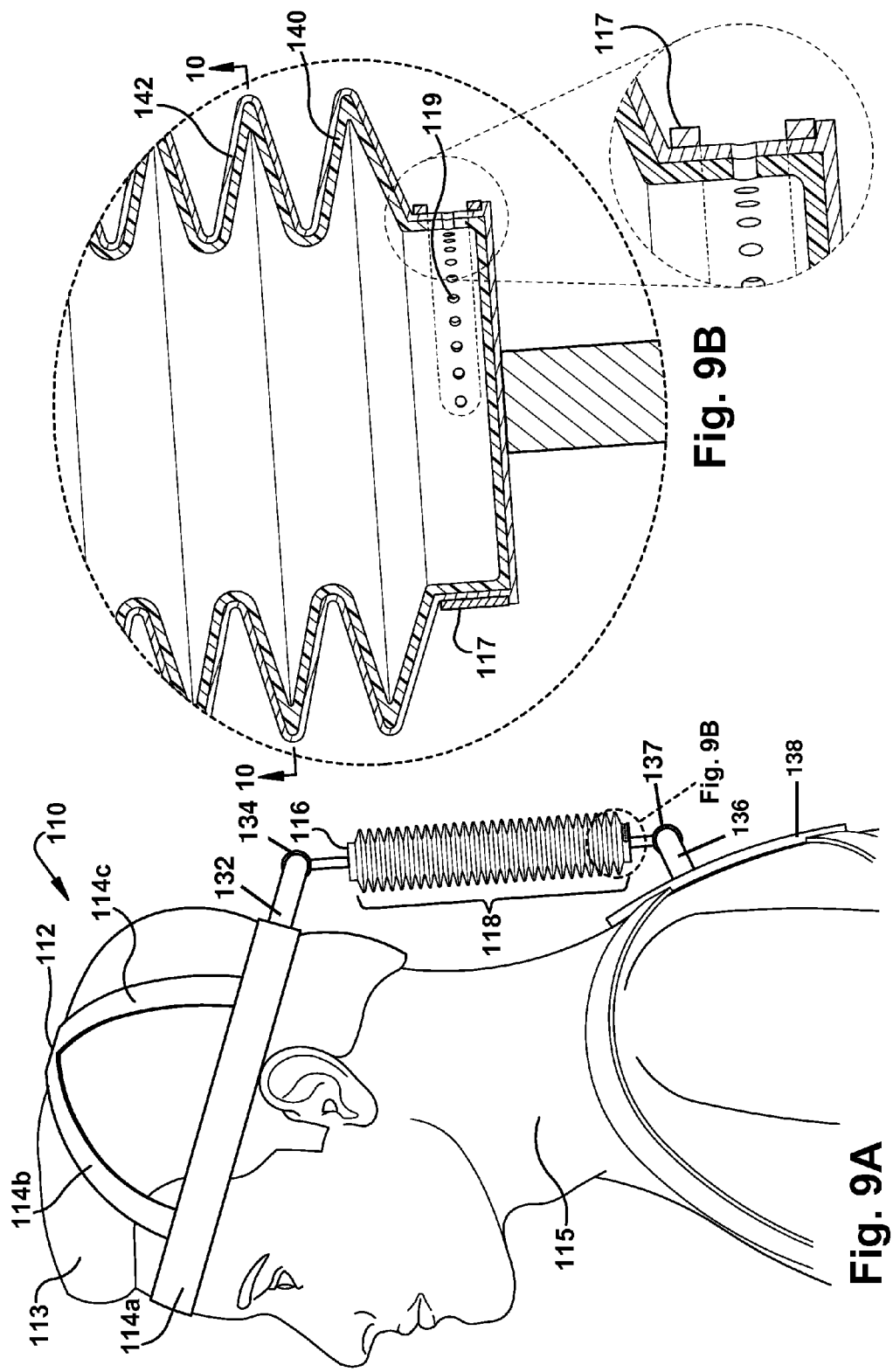
FIG. 9A shows a side view of an embodiment of a device of the present disclosure in a neutral position on a user. The device includes a headpiece, a support harness and a telescoping member having expansion bellows.
FIG. 9B shows an exploded view of the telescoping member of FIG. 9A. The inset shows a close-up view of the relationship between the perforated portions of the telescoping member and the outer circular member. The telescoping member includes perforated portions allowing entry and exit of fluid into and out of the telescoping member and an outer circular member for controlling the entry and exit of fluid through the perforated portions.

An embodiment of a device 110 of the present disclosure for reducing brain and cervical spine injury is shown in FIG. 9A. The device 110 includes a headpiece 112 for securing to a person's head 113. The headpiece 112 may be a harness or a conventional helmet such as is described in FIG. 2A. In an embodiment, the headpiece 112 may be a head harness composed of interconnected straps 114a, 114b, and 114c, like those shown in FIG. 2A. As shown in FIG. 9A, there may be one strap 114a, positioned circumferentially about the head, and two straps 114b and 114c, positioned in a criss-cross manner on top of the head 113. In an embodiment, the headpiece 112, designed as a head harness, a helmet or any other similar type device, is sufficiently designed to only secure to a user's head and does not need to be secured to any other components such as, for example, components of a moving vehicle or training gear, to produce the desired protection. The device 110 includes an accordion-like telescoping member 116 having expansion bellows 118 with convolutions that control the air which makes the accordion-like telescoping member 116 extend and compress. The bellows 118 allow for compression and expansion and little bending. In an embodiment, the bellows 118 are made from materials that allow the accordion-like telescoping member 116 to compress without bending. Examples of materials suitable for construction of the bellows 118 include, but are not limited to, plastics, steels, alloys or any other light weight materials that do not bend easily. Examples of materials suitable for the bellows 118 include, but are not limited to, stainless steel, alloys such as Inconel, Monel, Titanium and 316 stainless steel. The bellows 118 may be circular, triangular, square-shaped or any other shape as the present disclosure is not intended to be limited in this manner.

Figure 10:
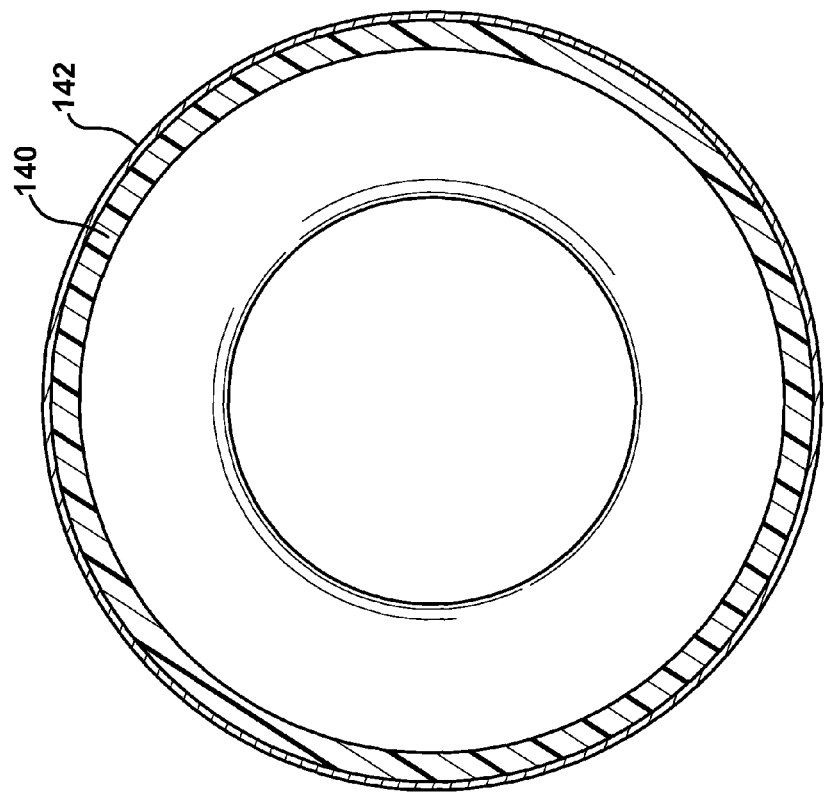
FIG. 10 shows a cross-sectional view of the telescoping member of FIG. 9B taken along line 10-10.

FIG. 9B in conjunction with FIG. 10 show close-up cut-away views of the accordion-like telescoping member 116. In an embodiment, the bellows 118 are formed from at least one inner layer 140 and at least one outer layer 142. In an embodiment, the layers 140 and 142 are airtight. The inner layer 140 may be fabricated from a material that is gas-tight and pliable, such as Gortex, polyethylene or any other similar material. The outer layer 142 may be made out of plastic, steel, metal or any other material as the present disclosure is not intended to be limited in this manner. The chamber forming the bellows 118 of the accordion-like telescoping member 116 may be filled with air, liquid, solid, gas or any other substance.

Perforated portions 119 of the accordion-like telescoping member 116 allow entrance and exit (intake/outflow) of fluid during extension and compression of the accordion-like telescoping member 116 into the airtight chamber. In an embodiment, the fluid powering the telescoping member 116 is a gas. In an embodiment, the gas is air. In an embodiment, the fluid powering the telescoping member 116 is a liquid. In an embodiment, the liquid is a hydraulic liquid. The perforated portions 119 may be variably exposed by an overriding outer circular member 117. The outer circular member 117 can expose more or less of the perforated portions 119 as needed at the base of the accordion-like telescoping member 116. In an embodiment, the outer circular member 117 can be controlled manually by turning the outer circular member 117 and exposing more or less of the perforated portions 119. In an embodiment, the outer circular member 50 can be controlled electronically. In an embodiment, the outer circular member 117 may be completely closed where no air may enter or exit or may be entirely open where air may enter and exit.

In an embodiment, the outer circular member 117 is controlled electronically to expose more or less of the perforated portions 119. In such embodiments, the outer circular member 117 can be controlled by an acceleration sensor arrangement comprising an acceleration threshold detector for detecting external forces experienced by the user's head to determine acceleration of the user's head and for providing an output signal; and a processor for receiving the output signal and generating an event signal to trigger the intake or outflow of fluid by the telescoping member 116 by moving the outer circular member 117 to expose more or less of the perforated portions 119. In an embodiment, the acceleration threshold detector provides an output signal having a first value when the acceleration is less than a predetermined threshold and is arranged to switch the output signal from the first value to a second value when the acceleration reaches the predetermined threshold. The processor generates an event signal to trigger movement of the outer circular member 117 to expose more or less of the perforated portions 119, in response to the output signal from the acceleration threshold detector switching to the second value. In an embodiment, the acceleration threshold detector comprises at least one of a piezo element and a micromachined element. In an embodiment, the acceleration threshold detector is a Piezoresisitive 3-Axis acceleration sensor adapted to trigger an event (such as the intake or outflow or air by the telescoping member) when all outputs from X, Y or Z go below a predetermined set threshold. In an embodiment, the acceleration threshold detector is a MEMS accelerometer. A programmable sequence can control the movement of the outer circular member 117 to expose more or less of the perforated portions 119 such that at the predetermined threshold of acceleration there is a shut off of the fluid portal followed by a rapid release and then closure, repeating hundreds of times per second causing an oscillatory slowing of the acceleration to a full stop. If the head movement exceeds the set threshold then there is a rapid deceleration to return the movement to below threshold acceleration. Once set at a threshold, an accelerometer can activate the locking device in a lockable gas spring piston damper or the damping device in a dynamic gas spring piston damper. In an embodiment, the accelerometer may be set at a threshold of about 20 g or less or 3000 rads/second squared or less. Setting the accelerometer at this threshold may aid in preventing or ameliorating the chances of sustaining a concussion. In an embodiment, a pressure sensor integrator (rate of pressure increase and decrease) or air velocity measurement may be used in conjunction with the telescoping member 116 to set various thresholds to activate the locking device in a lockable gas spring piston damper or the damping device in a dynamic gas spring piston damper. In an embodiment, the device 110 may include an acceleration threshold detector with a set acceleration threshold and an electronic shut-off valve. In an embodiment, the acceleration threshold detector may be located on the front at a point between the eyes and mid forehead to detect acceleration in the coronal, sagittal and axial planes. When located vertically on the front, the acceleration threshold detector may detect acceleration on the sagittal plane. When located horizontally on the front, the acceleration threshold detector may detect acceleration on the axial plane. In an embodiment, the acceleration threshold detector may be located vertically at a point above the ear. This location may allow acceleration to be detected in the coronal plane.

The telescoping member 116 is sufficiently designed for extension and compression in a linear plane, and includes a first engaging member or connector 134 for engaging the first attachment member 132 of the headpiece 112, and a second engaging member or connector 137 for engaging an attachment member 136 of a support harness 138. In an embodiment, the connector 134 is a universal joint, allowing free movement in at least 180 degrees so that the telescoping member 116 remains linear. In an embodiment, the connector 134 and the first attachment member 132 attach to the strap 114a at the back of the head 113 at approximately the level of the inion. The inion represents the middle of the back of the head 113 and additionally is located equidistantly from bottom of skull to top. In an embodiment, the connector 134 of the telescoping member 116 can attach to a helmet at approximately the bottom base. The connector 134 may be detachable or removable from the first attachment member 132. The connector 134 may be fabricated from a joint, a hinge, a socket or any other device for coupling the headpiece 112 to the telescoping member 116 and allowing movement in more than one plane. In an embodiment, the connector 134 and the first attachment member 132 form a ball and socket joint allowing three degrees of freedom, permitting rotary movement in all directions through the movement of the connector 134 in the first attachment member 132. In such embodiments, the connector 134 terminates in a ball, and the first attachment member 132 terminates in a spherical shell sized to snugly envelope the ball of the connector 134. When the ball of the connector 134 is within the socket of the first attachment member 132, the centers of the ball and socket are coincident, resulting in a spherical geometry that facilitates full three dimensional rotation of the connector 134 and the first attachment member 132 about the coincident centers. In an embodiment, the ball and socket joint provides multi-axial and multi-directional positioning of the head. In an embodiment, the ball and socket joint allows free movement of the telescoping member 116 such that the telescoping member 116 remains in straight alignment and does not bend. In an embodiment, the connector 134 is made from a pliable material.

In an embodiment, the support harness 138 includes a vest or plate portion and straps sufficiently designed to secure to the user's torso. In an embodiment, the support harness may include a chest vest. In an embodiment, the support harness 138, designed as a vest, a plate or any other similar type device, is sufficiently designed to only secure to a user's torso and does not need to be secured to any other components such as, for example, components of a moving vehicle or sports training gear, to produce the desired protection. In an embodiment, the connector 37 attaches to the support harness 138 at the level of the C7/T1 spinous processes. The C7/T1 spinous processes represents the top or the torso and the base of the neck 115. In an embodiment, the support harness 138 includes a vest and/or a plate connecting a ball joint at approximately the level of the first thoracic spinous process. In an embodiment, the connector 137 can attach to a car seat in a vehicle that the user is in. The connector 137 may be detachable or removable from the second attachment member 136. The connector 137 may be fabricated from a joint, a hinge, a socket or any other device for coupling the support harness 138 to the telescoping member 116 and allowing movement in more than one plane. In an embodiment, the connector 137 and the second attachment member 136 form a ball and socket joint allowing three degrees of freedom, permitting rotary movement in all directions through the movement of the connector 137 in the second attachment member 136. In such embodiments, the connector 137 terminates in a ball, and the second attachment member 36 terminates in a spherical shell sized to snugly envelope the ball of the connector 137. When the ball of the connector 137 is within the socket of the second attachment member 136, the centers of the ball and socket are coincident, resulting in a spherical geometry that facilitates full three dimensional rotation of the connector 137 and the second attachment member 136 about the coincident centers. In an embodiment, the ball and socket joint provides multi-axial and multi-directional positioning of the head. In an embodiment, the ball and socket joint allows free movement of the telescoping member 116 such that the telescoping member 116 remains in straight alignment and does not bend. In an embodiment, the connector 137 is made from a pliable material.

Figure 11:
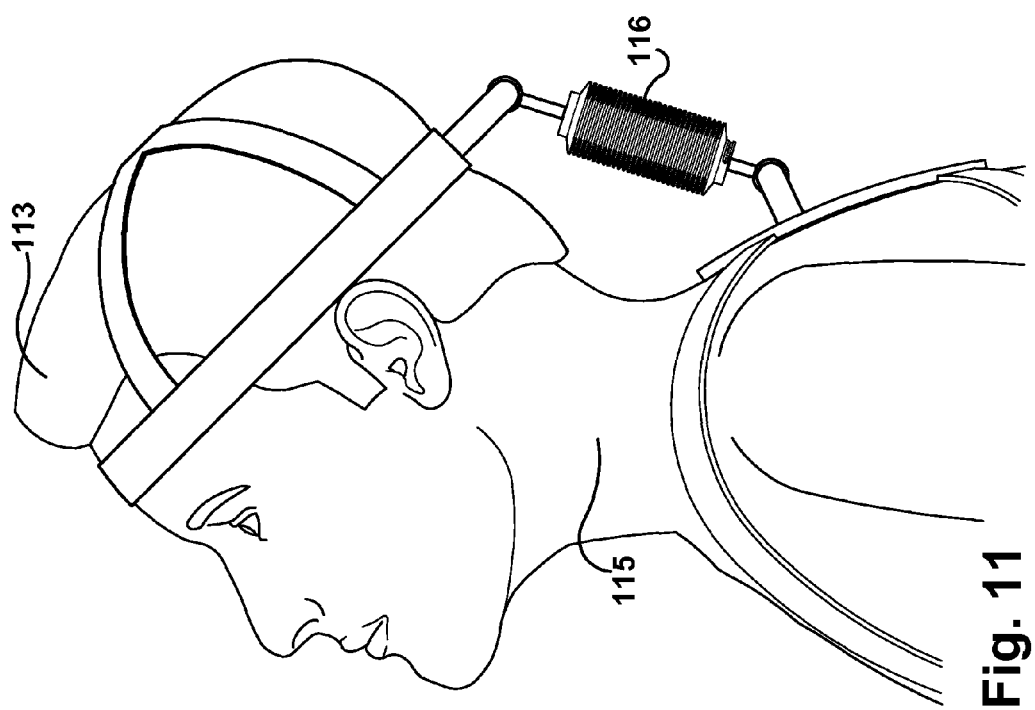
FIG. 11 shows a side view of the device of FIG. 9A on the user. The telescoping member is in a fully compressed state.

Similar to the telescoping member 28 of FIG. 2A, the accordion-like telescoping member 116 may compress the distance between the inion and first thorasic spinous process when the head 113 is fully extended, which is approximately two inches, and may extend the distance of about 8 inches between the inion and first thorasic spinous process when the head 113 is fully in flexion, which is approximately eight inches. In an embodiment, the accordion-like member 116 may include a collapsible and extendible tube. In an embodiment, the accordion-like member 116 may include a collapsible and extendible tube with a locking device. In an embodiment, the accordion-like member 116 may include an internal collapsible and extendible tube adapted to keep the accordion-like member 116 from bending. FIG. 11 shows the accordion-like telescoping member 116 in a fully compressed state where the head 113 and neck 115 are extended.

Figure 12:
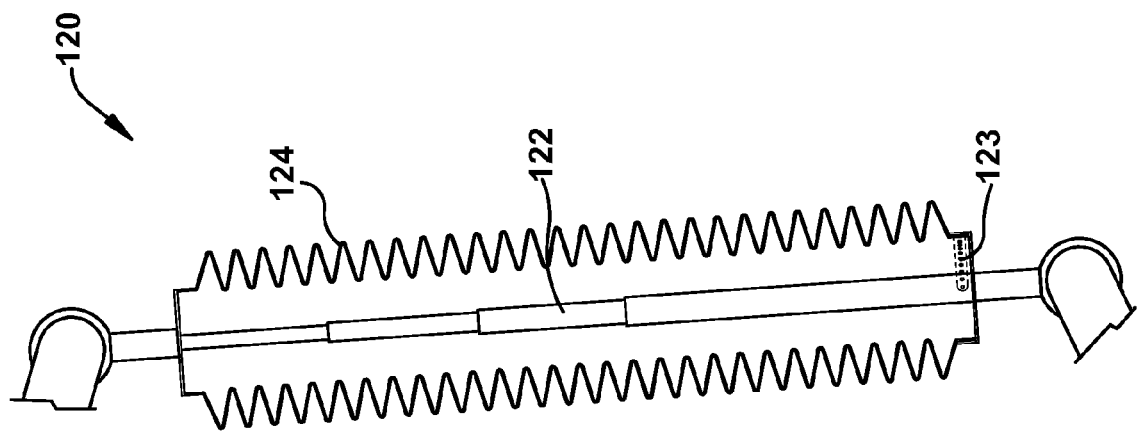
FIG. 12 shows a side view of an embodiment of a telescoping member of the present disclosure in a fully extended state.

FIG. 12 shows an embodiment of a telescoping member 120 of the present disclosure that can be used with a head harness and a support harness, as described above, to form a device of the present disclosure. The telescoping member 120 includes an inner telescoping member 122 situated inside of an outer accordion-like telescoping member 124. The inner telescoping member 122 acts to prevent bending of the outer accordion-like telescoping member 124 and to allow the outer accordion-like telescoping member 124 to remain in straight alignment with the headpiece of the device. In an embodiment, the outer accordion-like telescoping member 124 includes all or some of the features of the accordion-like telescoping member 116.

A device of the present disclosure can be used to prevent injuries that may occur, for example, during a vehicle crash, a sports accident, during battle and from a fall. Injuries that can be prevented include, but are not limited to, traumatic brain injury (TBI), cervical spine injuries, cervical spinal cord injuries, and cervical spine ligamentous injuries, among others. Symptomatic, non-penetrating brain injury, such as cervical spine and spinal cord injury, would be eliminated or markedly reduced with a device of the present disclosure. In an embodiment, a device of the present disclosure can reduce the incidence of brain, cervical spine, and spinal cord injury in crash victims, athletes, military and others while providing unencumbered head motion and range during normal circumstances.

TBI is a global health problem in terms of incidence, cost, and impact on daily living. Worldwide, an estimated 57 million individuals have been hospitalized with TBI. In the United States, medical center emergency rooms report approximately 1.74 million cases of mild TBI. These estimates fail to include unrecognized or unreported TBI cases that may number up to 3 million for sports-related injuries and up to 40% for personnel participating in current military engagements. The type, direction, intensity, and duration of forces all contribute to the characteristics and severity TBI. Forces that may contribute to TBI include angular, rotational, shear, and translational forces A common pathway of injury is diffuse axonal injury (DAI), which is one of the most common and devastating types of TBI. DAI results from rotational shear forces that tear white matter tracts. Acceleration/deceleration TBI studies in animals and clinical investigations have attributed cognitive deficits to DAI. Distinguished from focal contusion without shearing, DAI is defined as damage to axons at the gray/white matter junction of the cerebral hemispheres, corpus callosum and dorsolateral midbrain and often involves the superior cerebellar peduncles. These deep white matter abnormalities can be detected by a MRI and are associated with poorer neuropsychological test performances and poor long-term outcome.

DAI disrupts attention and working memory networks by severing the connections in anterior white matter tracts that connect brain areas that carry out these functions and can also affect motor coordination. This disruption results in impaired timing on cognitive tasks, which is manifested as difficulty conversing, problem solving, regulating emotions and navigating daily activities-cognitive coordination problems. These difficulties can put those injured and others in immediate harm's way and lead to long term, persistent, unrecognized daily interaction problems. Similar to DAI, injuries to the cervical spine, ligaments and spinal accord occur mainly with rapid flexion and extension or torque of the neck.

The perforated portions of a telescoping member of the present disclosure may be variably exposed by the overriding rotatable circular member surrounding the outer diameter of the telescoping member. The outer circular member can expose more or less of the perforated portions as needed at the base of the telescoping member. In a situation where a user may experience a sudden impact which may ordinary (without use of a device of the present disclosure) lead to hyper-extension, hyper-flexion or hyper-angulation of the neck causing injury to the brain, cervical spine, and spinal cord, a user wearing a device of the present disclosure can reduce the incidence of hyper-extension, hyper-flexion or hyper-angulation of the neck preventing or substantially reducing injury to the brain, cervical spine, and spinal cord. In an embodiment, when the head and neck move from a neutral position to a flexed position (chin to chest direction) due to an injury, a telescoping member of the present disclosure is adapted to have a set threshold acceleration such that if the acceleration experienced by the user, which can be determined by an acceleration threshold detector in communication with the telescoping member or set by the number of perforated portions exposed at the base of the telescoping member, exceeds the set threshold acceleration, the telescoping member will stop extending initially, causing the head and neck to stop moving. This can immediately be followed by a release caused either by the fluid escaping under a lower acceleration through the set number of perforated portions or an electronically programmed series of releases guided by the acceleration threshold detector. In an embodiment, when the head and neck move from a neutral position to an extended position (head moves backward) due to an injury, a telescoping member of the present disclosure is adapted to have a set threshold acceleration such that if the acceleration experienced by the user, which can be determined by an acceleration threshold detector in communication with the telescoping member or set by the number of perforated portions exposed at the base of the telescoping member, exceeds the set threshold acceleration, the telescoping member will stop compressing initially, causing the head and neck to stop moving. This can be followed immediately by a release caused either by the fluid escaping under a lower acceleration through the set number of perforated portions or an electronically programmed series of releases guided by the acceleration threshold detector. In an embodiment, a device of the present disclosure prevents whip-lashing, thus preventing brain and cervical injury. In an embodiment, a device of the present disclosure protects the brain and cervical spine from a whiplash effect of the head in all directions (axes). The telescoping member of a device of the present disclosure remains in linear alignment due to the swiveling of the ball and socket joints.

In an embodiment, a device of the present disclosure stops movement immediately when acceleration or deceleration meets a certain set threshold which accordingly restricts the free flow of fluid. In an embodiment, an acceleration threshold detector adapted to determine the acceleration of a user's head provides an output signal to a processor and generates an event signal to indicate that the set threshold has been reached. In an embodiment, the number of perforated portions exposed at the base of the telescoping member sets the acceleration threshold. Following the immediate stop, the acceleration or deceleration drops below the set threshold allowing the free flow of fluid once again. In an embodiment, an acceleration threshold detector in tandem with a control mechanism of the rotatable circular member is programmed to analyze an input acceleration or deceleration and provide a signal to the control mechanism to expose or close a desired amount of the perforated portions. Movement may once again be restricted if the force which caused the initial acceleration or deceleration persists. In such a manner, a force applied to the head, such as in a blow to the head, will cause the head to move rapidly above a set threshold causing immediate restriction of movement but then releasing and restricting again as the head continues to be affected by the accelerating force. The net effect is a rapid stopping of movement followed by a series of stops and goes determined by the net accelerating/decelerating force and the number of perforated portions exposed or the accelerometer programming. In such a manner, the head and neck do not come to a sudden and complete stop, but rather a stop followed immediately by a rapid series of short releases and stops which will bring the head slowly to a halt. This dampening of the movement following the stop ensures that the brain and cervical spine never come to a rapid final stop causing strain in the neural tissues and surrounding supporting structures, but rather a stop followed by release and then dampening the reduction of movement over time.

A method for preventing brain and cervical spine injury includes positioning a device on a user, the device including a headpiece sufficiently designed to secure to a head of the user, the headpiece having an attachment member; a support harness sufficiently designed to secure to a torso of the user, the support harness having an attachment member; and a telescoping member sufficiently designed for extension and compression in a linear plane, the telescoping member having a first engaging member for engaging the attachment member of the headpiece, and a second engaging member for engaging the attachment member of the support harness; and setting a fixed acceleration threshold for the device, the fixed acceleration threshold representing a maximum acceleration for free movement of the user's head.

A person wearing a device of the present disclosure will have voluntary free head movement with respect to the torso. This voluntary movement is achieved by the telescoping member extending and compressing with minimal resistance when the head moves in any direction including the coronal, sagittal, and axial planes. The connector at each end of the telescoping member ensures that the member extends and compresses in a linear plane without bending.

In an embodiment, an inner airtight membrane of a telescoping member of the present disclosure fills with fluid on extension and exhausts fluid when the telescoping member compresses. The perforated portions of a telescoping member of the present disclosure are adapted to be in fluid communication with an opening in the airtight membrane allowing fluid to enter and exit the interior of the airtight membrane. The net surface area for fluid entry and exit may allow fluid movement easily at voluntary head movement speeds. Although the perforated portions are shown positioned at the base of the telescoping member, other locations for openings may be possible.

When a person wearing a device of the present disclosure is subjected to an external force such as a direct impact with resultant high acceleration or rapid deceleration such as in a car crash, the device may reduce the movement in a pattern that will decrease the brain tissue strain. Since a significant part of traumatic brain injury is the strain and resultant tearing of brain tissue from rapid acceleration or deceleration, a reduction in this strain force may lessen brain damage. A telescoping member of a device of the present disclosure will respond to rapid movement by extending or compressing, depending on the direction of the external force. The rapidity of the extension or compression will be limited by the rapidity of fluid intake (extension of the member) or rapidity of fluid exhaust (compression of the member) into and out of the airtight membrane, respectively. Therefore, the resistance to above normal head movement is by the extension or compression of the telescoping member determined by the resistance of fluid intake and fluid exhaust into and out of the interior of the airtight membrane.

The threshold for reducing above normal head movement may be changed by adjusting the surface area for fluid entry and exit. In an embodiment, a telescoping member of the present disclosure includes perforations that communicate with the interior of an airtight membrane. The surface area of the perforations can be increased or decreased by having an outer sliding or rotating circular member that can variable expose more or less perforations. When the rotating circular member is completely turned no perforations are exposed and the airtight membrane will not have fluid entry or exit and the telescoping member will not be able to extend or compress at all leading to no movement of the head. As the rotating circular member turns, revealing more perforations the threshold for resistance to rapid movement decreases allowing head movement. The person will be able to adjust the surface area of perforations to set a preferred threshold level.

A method for preventing brain and cervical spine injury includes providing a device comprising a headpiece sufficiently designed to secure to the user's head, the headpiece having a first attachment member; a support harness sufficiently designed to secure to the user's torso, the support harness having a second attachment member; an acceleration threshold device sufficiently designed to detect external forces experienced by the user's head and for providing an output signal to a processor circuit; and a telescoping member adapted to extend and compress in a linear plane by the intake and outflow of fluid, wherein the telescoping member has a first engaging member for engaging the first attachment member, the first engaging member and the first attachment member forming a ball and socket joint adapted to allow three degrees of freedom, permitting rotary movement in all directions through the movement of the first engaging member in the first attachment member, and wherein the telescoping member has a second engaging member for engaging the second attachment member, the second engaging member and the second attachment member forming a ball and socket joint adapted to allow three degrees of freedom, permitting rotary movement in all directions through the movement of the second engaging member in the second attachment member; connecting the first engaging member of the telescoping member with the first attachment member of the headpiece approximately at a level of the user's inion; connecting the second engaging member of the telescoping member with the second attachment member of the support harness approximately at a level of the user's C7/T1 spinous processes; detecting, using an acceleration threshold detector, external contact forces experienced by the user's head to determine acceleration of the user's head; providing, using the acceleration threshold detector, an output signal representing if the determined acceleration experienced by the user's head reached a predetermined threshold; receiving, using a processor, the output signal from the acceleration threshold detector; and generating, using the processor, an event signal to trigger the intake or outflow of fluid by the telescoping member in response to the determined acceleration. In an embodiment, the telescoping member has a main tube and a series of progressively smaller diameter tubes nested within each other. In an embodiment, the telescoping member has expansion bellows. In an embodiment, the telescoping member includes perforated portions allowing entrance and exit of fluid to and from the telescoping member during extension and compression of the telescoping member. In an embodiment, the fluid is a gas. In an embodiment, the fluid is a liquid. In an embodiment, an airtight membrane in fluid communication with the perforated portions covers an inside surface of the telescoping member and is adapted to house the fluid. In an embodiment, a rotatable circular member circumferentially surrounds an outer diameter of the telescoping member and is adapted to control the entrance and exit of fluid through the perforated portions. In an embodiment, the rotatable circular member is controlled by an accelerometer with a set threshold and a programmable sequence.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device comprising:
    a headpiece sufficiently designed to secure to a user's head, the headpiece having a first attachment member;
    a support harness sufficiently designed to secure to the user's torso, the support harness having a second attachment member; and
    a telescoping member adapted to linearly extend and compress by a respective ingress or egress of fluid,
    wherein the telescoping member includes perforated portions adapted to allow the ingress and egress of fluid during extension and compression of the telescoping member, and wherein a rotatable circular member circumferentially surrounds an outer diameter of the telescoping member and is adapted to control the ingress and egress of fluid through the perforated portions, wherein the telescoping member has a first engaging member for engaging the first attachment member, and wherein the telescoping member has a second engaging member for engaging the second attachment member, wherein the first engaging member and the first attachment member form a ball and socket joint adapted to allow three degrees of freedom, permitting rotary movement in all directions through the movement of the first engaging member in the first attachment member, and wherein the second engaging member and the second attachment member form a ball and socket joint adapted to allow three degrees of freedom, permitting rotary movement in all directions through the movement of the second engaging member in the second attachment member.

2. The device of claim 1 wherein the fluid is a gas.

3. The device of claim 2 wherein the gas is air.

4. The device of claim 1 wherein the fluid is a liquid.

5. The device of claim 4 wherein an airtight membrane in fluid communication with the perforated portions covers an inside surface of the telescoping member and is adapted to house the liquid.

6. The device of claim 1 wherein the rotatable circular member is controlled electronically to expose more or less of the perforated portions.

7. A device comprising:
   a headpiece sufficiently designed to secure to a user's head, the headpiece having a first attachment member;
   a support harness sufficiently designed to secure to the user's torso, the support harness having a second attachment member; and
   a telescoping member having expansion bellows adapted to linearly extend and compress by an ingress or egress of fluid,
   wherein the telescoping member includes perforated portions adapted to allow the ingress and egress of fluid during extension and compression of the telescoping member, and wherein a rotatable circular member circumferentially surrounds an outer diameter of the telescoping member and is adapted to control the ingress and egress of fluid through the perforated portions,
   wherein the telescoping member has a first engaging member for engaging the first attachment member, and
   wherein the telescoping member has a second engaging member for engaging the second attachment member,
   wherein the first engaging member and the first attachment member form a ball and socket joint adapted to allow three degrees of freedom, permitting rotary movement in all directions through the movement of the first engaging member in the first attachment member, and wherein the second engaging member and the second attachment member form a ball and socket joint adapted to allow three degrees of freedom, permitting rotary movement in all directions through the movement of the second engaging member in the second attachment member.

8. The device of claim 7 wherein the fluid is a gas.

9. The device of claim 8 wherein the gas is air.

10. The device of claim 7 wherein the fluid is a liquid.

11. The device of claim 10 wherein an airtight membrane in fluid communication with the perforated portions covers an inside surface of the telescoping member and is adapted to house the fluid.

12. The device of claim 7 wherein the rotatable circular member is controlled electronically to expose more or less of the perforated portions.

13. A method for preventing brain and cervical spine injury to a user comprising: providing a device comprising:
   a headpiece sufficiently designed to secure to the user's head, the headpiece having a first attachment member;
   a support harness sufficiently designed to secure to the user's torso, the support harness having a second attachment member;
   an acceleration threshold device sufficiently designed to detect external forces experienced by the user's head and for providing an output signal to a processor to trigger an event; and
   a telescoping member adapted to linearly extend and compress by an ingress or egress of fluid,
   wherein the telescoping member includes perforated portions adapted to allow the ingress or egress of fluid during extension and compression of the telescoping member and wherein the event signal triggers movement of a rotatable circular member to expose more or less of the perforated portions,
   wherein the telescoping member has a first engaging member for engaging the first attachment member, the first engaging member and the first attachment member forming a ball and socket joint adapted to allow three degrees of freedom, permitting rotary movement in all directions through the movement of the first engaging member in the first attachment member, and
   wherein the telescoping member has a second engaging member for engaging the second attachment member, the second engaging member and the second attachment member forming a ball and socket joint adapted to allow three degrees of freedom, permitting rotary movement in all directions through the movement of the second engaging member in the second attachment member;
   connecting the first engaging member of the telescoping member with the first attachment member of the headpiece approximately at a level of the user's inion;
   connecting the second engaging member of the telescoping member with the second attachment member of the support harness approximately at a level of the user's C7/T1 spinous processes;
   detecting, using an acceleration threshold detector, external contact forces experienced by the user's head to determine acceleration of the user's head;
   providing, using the acceleration threshold detector, an output signal representing if the determined acceleration experienced by the user's head reached a predetermined threshold;
   receiving, using a processor, the output signal from the acceleration threshold detector; and
   generating, using the processor, an event signal to trigger the intake or outflow of fluid by the telescoping member in response to the determined acceleration.

14. The method of claim 13 wherein the fluid is selected from one of a gas or a liquid.

* * * * *